United States Patent [19]

Eistetter et al.

[11] 4,430,339

[45] Feb. 7, 1984

[54] SUBSTITUTED OXIRANECARBOXYLIC ACIDS, THEIR PREPARATION AND THEIR USE AS MEDICAMENTS

[75] Inventors: Klaus Eistetter, Konstanz; Erich Rapp, Radolfzell, both of Fed. Rep. of Germany

[73] Assignee: Byk Gulden Lomberg Chemische Fabrik Gesellschaft mit beschränkter Haftung, Konstanz, Fed. Rep. of Germany

[21] Appl. No.: 371,294

[22] PCT Filed: Aug. 24, 1981

[86] PCT No.: PCT/EP81/00137

§ 371 Date: Apr. 6, 1982

§ 102(e) Date: Apr. 6, 1982

[87] PCT Pub. No.: WO82/00822

PCT Pub. Date: Mar. 18, 1982

[30] Foreign Application Priority Data

Aug. 29, 1980 [DE] Fed. Rep. of Germany ....... 3032668
Feb. 25, 1981 [CH] Switzerland .......................... 1243/81

[51] Int. Cl.$^3$ ............................................. C07D 303/48
[52] U.S. Cl. ...................................... 424/278; 549/549
[58] Field of Search ................. 549/549, 560; 424/278

[56] References Cited

U.S. PATENT DOCUMENTS 4,196,300  4/1980  Mohrbacher et al. .............. 549/549

Primary Examiner—Norma S. Milestone
Attorney, Agent, or Firm—Berman, Aisenberg & Platt

[57] ABSTRACT

Epoxycycloalkylalkanecarboxylic acids of the general formula I

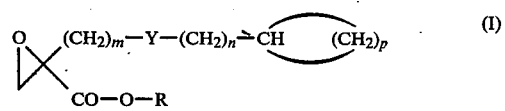

wherein R denotes a hydrogen atom or a lower alkyl group, Y denotes an oxygen atom (—O—) or a methylene group (—CH$_2$—), m denotes an integer from 0 to 6, n denotes an integer from 0 to 6 and p denotes an integer from 2 to 11 (and m cannot be 0 or 1 if Y represents an oxygen atom, and the sum of the numbers m, n and p is an integer from 6 to 15), and also the salts of the carboxylic acids, are new compounds. They exhibit a hypoglycaemic action on warmblooded animals. Processes for the preparation of the new compounds are described.

13 Claims, No Drawings

SUBSTITUTED OXIRANECARBOXYLIC ACIDS, THEIR PREPARATION AND THEIR USE AS MEDICAMENTS

The invention relates to epoxycycloalkylalkanecarboxylic acids, processes for their preparation, their use and medicaments containing them.

The compounds according to the invention are used in the pharmaceutical industry as intermediate products and for the preparation of medicaments.

The invention relates to epoxycycloalkylalkanecarboxylic acids of the general formula I

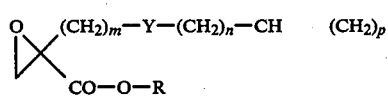

wherein R denotes a hydrogen atom or a lower alkyl group, Y denotes an oxygen atom (—O—) or a methylene group (—CH$_2$—), m denotes an integer from 0 to 6, n denotes an integer from 0 to 6 and p denotes an integer from 2 to 11 (and m cannot be 0 or 1 if Y represents an oxygen atom, and the sum of the numbers m, n and p is an integer from 6 to 15), and to the salts of the carboxylic acids; or to epoxycycloalkylalkanecarboxylic acids of the general formula (Ia)

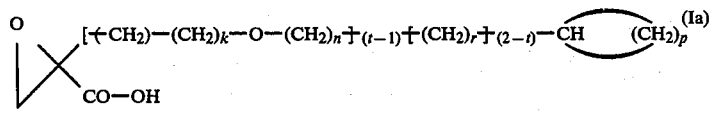

wherein
k is an integer from 1 to 5, inclusive,
n is an integer from 0 to 6, inclusive,
p is an integer from 2 to 11, inclusive,
t is a positive whole number of at most 2,
r is an integer from 1 to 13, inclusive,
the sum of k, n and p being an integer of from 5 to 14, and the sum of r and p being an integer of from 7 to 16,
lower alkyl esters and salts thereof.

Suitable lower alkyl groups are straight-chain or branched alkyl radicals having 1 to 4 carbon atoms: straight-chain alkyl radicals are the methyl, ethyl, n-propyl and n-butyl radicals, of which the methyl radical and the ethyl radical are preferred. Examples of branched alkyl radicals are the isopropyl, isobutyl and sec.-butyl radical, of which the isopropyl radical is preferred.

Suitable salts are salts with inorganic and organic bases. Pharmacologically unacceptable salts are converted by methods which are in themselves known into pharmacologically, that is to say biologically, acceptable salts, which are preferred amongst the salts according to the invention. Cations which are used for the formation of salts are above all the cations of the alkali metals, alkaline earth metals or earth metals; however, the corresponding cations of organic nitrogen bases, such as amines, aminoalkanols, amino-sugars, basic aminoacids and the like, are also used.

Examples which may be mentioned are the salts with lithium, sodium, potassium, magnesium, calcium, aluminium, ethylenediamine, dimethylamine, diethylamine, morpholine, piperidine, piperazine, N-lower alkyl-piperazines (for example N-methylpiperazine), methyl-cyclohexylamine, benzylamine, ethanolamine, diethanolamine, triethanolamine, tris-(hydroxymethyl)-aminomethane, 2-amino-2-methylpropanol, 2-amino-2-methyl-1,3-propanediol, glucamine, N-methylglucamine, glucosamine, N-methylglucosamine, lysine, ornithine, arginine and quinoline.

Epoxycycloalkylalkanecarboxylic acids of the general formula I*

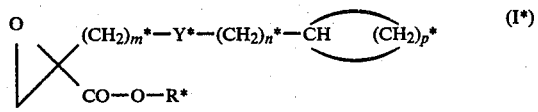

wherein R* denotes a hydrogen atom or a lower alkyl group, Y* denotes a methylene group (—CH$_2$—), m* denotes an integer from 1 to 6, n* denotes the number 1 and p* denotes an integer from 4 to 7 (and the sum of the numbers m*, n* and p* is an integer from 6 to 11), and also the salts of the carboxylic acids form an embodiment of the invention.

Epoxycycloalkylalkanecarboxylic acids of the general formula I**

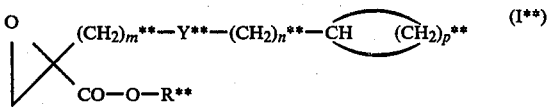

wherein R denotes a hydrogen atom or a lower alkyl group, Y denotes an oxygen atom (—O—), m denotes an integer from 2 to 6, n denotes an integer from 0 to 4 and p denotes an integer from 4 to 7 (and the sum of the numbers m, n and p is an integer from 6 to 11), and also the salts of the carboxylic acids form a further embodiment of the invention.

The following may be mentioned as examples of representatives of the compounds according to the invention: 2-(4-cyclohexylbutyl)-oxirane-2-carboxylic acid ethyl ester, 2-(5-cyclopropylpentyl)-oxirane-2-carboxylic acid methyl ester, 2-(3-cyclooctylpropyl)-oxirane-2-carboxylic acid ethyl ester, 2-(8-cyclopentyloctyl)-oxirane-2-carboxylic acid methyl ester, 2-(2-cycloundecylethyl)-oxirane-2-carboxylic acid n-propyl ester, 2-(3-cyclododecylpropyl)-oxirane-2-carboxylic acid ethyl ester, 2-(6-cyclohexylhexyl)-oxirane-2-carboxylic acid n-butyl ester, 2-(10-cyclopentyldecyl)-oxirane-2-carboxylic acid ethyl ester, 2-(2-cycloheptylethyl)-oxirane-2-carboxylic acid isopropyl ester, 2-(7-cyclobutylheptyl)-oxirane-2-carboxylic acid methyl ester, 2-cyclononylmethyl-oxirane-2-carboxylic acid sec.-butyl ester, 2-(9-cyclopropylnonyl)-oxirane-2-carboxylic acid methyl ester, 2-(3-cyclodecylpropyl)-oxirane-2-carboxylic acid n-butyl ester, 2-cyclododecylmethyl-oxirane-2-carboxylic acid ethyl ester, 2-(5-cyclohexylpentyl)-oxirane-2-carboxylic acid n-propyl ester, 2-(4-cyclooctylbutyl)-oxirane-2-carboxylic acid methyl ester, 2-(4-cyclopentylbutyl)-oxirane-2-carboxylic acid isopropyl ester, 2-(6-cycloheptylhexyl)-oxirane-2-carboxylic acid methyl ester, 2-(5-cyclobutylpentyl)-oxirane-2-carboxylic acid ethyl ester, 2-(5-cyclooctylpentyl)-oxirane-2-carboxylic acid n-propyl ester, 2-(7-cycloheptylheptyl)-oxirane-2-carboxylic acid methyl ester, 2-(5-cyclododecylpentyl)-oxirane-2-carboxylic acid ethyl ester, 2-(6-cyclooctylhexyl)-oxirane-2-carboxylic acid methyl ester, 2-(5-cycloheptylpentyl)-oxirane-2-carboxylic acid sec.-butyl ester, 2-(2-cyclohexylethyl)-oxirane-2-carboxylic acid ethyl ester, 2-(6-cyclopentylhexyl)-oxirane-2-carboxylic acid methyl ester, 2-(7-cyclohexylheptyl)-oxirane-2-carboxylic acid isopropyl ester, 2-(4-cyclobutylbutyl)-oxirane-2-carboxylic acid n-butyl ester, 2-(2-cyclononylethyl)-oxirane-2-carboxylic acid ethyl ester, 2-(4-cyclododecylbutyl)-oxirane-2-carboxylic acid methyl ester, 2-(6-cyclobutylhexyl)-oxirane-2-carboxylic acid isopropyl ester, 2-(7-cyclooctylheptyl)-oxirane-2-carboxylic acid methyl ester, 2-(2-cyclopentylethyl)-oxirane-2-carboxylic acid ethyl ester, 2-(8-cyclohexyloctyl)-oxirane-2-carboxylic acid n-propyl ester, 2-(4-cycloheptylbutyl)-oxirane-2-carboxylic acid methyl ester, 2-(7-cyclopentylheptyl)-oxirane-2-carboxylic acid methyl ester, 2-(6-cyclobutylhexyl)-oxirane-2-carboxylic acid ethyl ester, 2-(2-cyclooctylethyl)-oxirane-2-carboxylic acid n-propyl ester, 2-[3-(2-cyclohexylethoxy)-propyl]-oxirane-2-carboxylic acid ethyl ester, 2-[2-(3-cyclobutylpropoxy)-ethyl]-oxirane-2-carboxylic acid methyl ester, 2-[4-(2-cycloheptylethoxy)-butyl]-oxirane-2-carboxylic acid isopropyl ester, 2-[3-(3-cyclopentylpropoxy)-propyl]-oxirane-2-carboxylic acid n-butyl ester, 2-[3-(cyclohexyloxy)-propyl]-oxirane-2-carboxylic acid ethyl ester, 2-[6-(4-cyclopropylbutoxy)hexyl]-oxirane-2-carboxylic acid methyl ester, 2-[5-(cyclopentyloxy)-pentyl]-oxirane-2-carboxylic acid ethyl ester, 2-[2-(cyclooctylmethoxy)-ethyl]-oxirane-2-carboxylic acid isopropyl ester, 2-[3-(2-cyclononylethoxy)-propyl]-oxirane-2-carboxylic acid methyl ester, 2-[2-(cyclododecylmethoxy)-ethyl]-oxirane-2-carboxylic acid ethyl ester, 2-[6-(3-cyclopropylpropoxy)-hexyl]-oxirane-2-carboxylic acid n-butyl ester, 2-[5-(4-cyclobutylbutoxy)-pentyl]-oxirane-2-carboxylic acid ethyl ester, 2-[3-(2-cyclododecylethoxy)-propyl]-oxirane-2-carboxylic acid methyl ester, 2-[2-(6-cyclopentylhexyloxy)-ethyl]-oxirane-2-carboxylic acid n-propyl ester, 2-[6-(cyclohexylmethoxy)-hexyl]-oxirane-2-carboxylic acid isopropyl ester, 2-[5-(cycloheptyloxy)-pentyl]-oxirane-2-carboxylic acid methyl ester, 2-[3-(cycloundecyloxy)-propyl]-oxirane-2-carboxylic acid ethyl ester, 2-[4-(cyclooctylmethoxy)-butyl]-oxirane-2-carboxylic acid n-butyl ester, 2-[2-(5-cyclobutylpentyloxy)-ethyl]-oxirane-2-carboxylic acid ethyl ester, 2-[2-(cyclononylmethoxy)-ethyl]-oxirane-2-carboxylic acid n-propyl ester, 2-[5-(2-cycloheptylethoxy)-pentyl]-oxirane-2-carboxylic acid methyl ester, 2-[6-(2-cyclopropylethoxy)-hexyl]-oxirane-2-carboxylic acid isopropyl ester, 2-[3-(6-cyclopentylhexyloxy)-propyl]-oxirane-2-carboxylic acid methyl ester, 2-[4-(3-cyclohexylpropoxy)-butyl]-oxirane-2-carboxylic acid n-propyl ester, 2-[5-(cycloheptylmethoxy)-pentyl]-oxirane-2-carboxylic acid methyl ester, 2-[6-(cyclooctyloxy)-hexyl]-oxirane-2-carboxylic acid ethyl ester, 2-[4-(cyclononyloxy)-butyl]-oxirane-2-carboxylic acid sec.-butyl ester, 2-[2-(4-cyclohexylbutoxy)-ethyl]-oxirane-2-carboxylic acid methyl ester, 2-[4-(2-cyclopentylethoxy)-butyl]-oxirane-2-carboxylic acid ethyl ester, 2-[4-(cyclopentylmethoxy)-butyl]-oxirane-2-carboxylic acid isopropyl ester, 2-[5-(cyclohexyloxy)-pentyl]-oxirane-2-carboxylic acid ethyl ester, 2-[3-(3-cycloheptylpropoxy)-propyl]-oxirane-2-carboxylic acid methyl ester, 2-[3-(cyclododecyloxy)-propyl]-oxirane-2-carboxylic acid n-butyl ester, 2-[4-(2-cyclooctylethoxy)-butyl]-oxirane-2-carboxylic acid ethyl ester, 2-[2-(4-cycloheptylbutoxy)-ethyl]-oxirane-2-carboxylic acid methyl ester, 2-[2-(4-cyclopentylbutoxy)-ethyl]-oxirane-2-carboxylic acid isopropyl ester, 2-[2-(5-cyclohexylpentyloxy)-ethyl]-oxirane-2-carboxylic acid ethyl ester, 2-[6-(cycloheptyloxy)-hexyl]-oxirane-2-carboxylic acid isopropyl ester, 2-[2-(3-cyclooctylpropoxy)-ethyl]-oxirane-2-carboxylic acid n-butyl ester, 2-[2-(2-cyclohexylethoxy)-ethyl]-oxirane-2-carboxylic acid methyl ester, 2-[2-(2-cycloheptylethoxy)-ethyl]-oxirane-2-carboxylic acid isopropyl ester, 2-[4-(cycloheptyloxy)-butyl]-oxirane-2-carboxylic acid ethyl ester, 2-[2-(cyclooctyloxy)-ethyl]-oxirane-2-carboxylic acid methyl ester, 2-[3-(cyclopentyloxy)-propyl]-oxirane-2-carboxylic acid n-butyl ester, 2-[6-(cyclopentylmethoxy)-hexyl]-oxirane-2-carboxylic acid ethyl ester, the corresponding oxirane-2-carboxylic acids and their salts with inorganic and organic bases.

The epoxycycloalkylalkanecarboxylic acids of the general formula I and/or of the embodiments I* and I** possess a centre of chirality. The invention therefore includes both the racemates and the enantiomers and mixtures thereof.

The compounds according to the invention have valuable pharmacological properties which enable them to be exploited commercially. They have a strong hypoglycaemic and hypoketonaemic action, which is of a comparatively short duration.

Because of their advantageous activity, the epoxycycloalkylalkanecarboxylic acids, according to the invention, of the general formula I and/or of the embodiments I* and I** and also the pharmacologically acceptable salts are suitable for the treatment and prophylaxis, in human and veterinary medicine, of diseases caused by disturbances of the metabolism of glucose and fats. Examples of conditions which are treated are prediabetic conditions, for preventing the manifestation of diabetes, manifest diabetes, for example adult diabetes, labile diabetes in young people and all pathological conditions which are associated with a pathologically increased production of ketonic substances.

The invention also relates, therefore, to a process for combating the said diseases by administering the compounds according to the invention. The invention also relates to the use of the compounds according to the invention in combating the said diseases.

The invention further relates to medicaments containing one or more of the epoxycycloalkylalkanecarboxylic acids of the general formula I

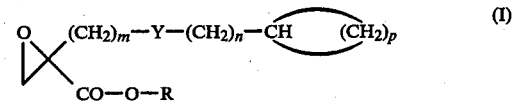

wherein R denotes a hydrogen atom or a lower alkyl group, Y denotes an oxygen atom (—O—) or a methylene group (—CH$_2$—), m denotes an integer from 0 to 6, n denotes an integer from 0 to 6 and p denotes an integer from 2 to 11 (and m cannot be 0 or 1 if Y represents an oxygen atom, and the sum of the numbers m, n and p is an integer from 6 to 15), and/or the pharmacologically acceptable salts of the acids with inorganic or organic bases.

Embodiments of the medicaments are those containing epoxycycloalkylalkanecarboxylic acids of the embodiments I* and I** and/or the pharmacologically acceptable salts of the acids with inorganic or organic bases.

The invention relates additionally to the use of the compounds according to the invention for the preparation of medicaments for combating the said diseases.

The medicaments are prepared in accordance with processes which are in themselves known. As medicaments, the new compounds can be used as such or, if appropriate, in combination with suitable pharmaceutical excipients. If the new pharmaceutical formulations contain pharmaceutical excipients in addition to the active compounds, the content of active compound in these mixtures is 1 to 95, preferably 15 to 85, percent by weight of the total mixture.

In accordance with the invention it is possible to use the active compounds in any desired form, for example a systemic form, in the field of human medicine, with the proviso that the formation and/or maintenance of adequate levels of active compounds in the blood or tissue is ensured. This can be achieved, for example, by oral or parenteral administration in suitable doses. The pharmaceutical formulation of the active compound is advantageously in the form of unit doses appropriate for the desired administration. unit dose can be, for example, a tablet, a dragee, a capsule, a suppository or a measured volume of a powder, of a granular material, of a solution, of an emulsion or of a suspension.

"Unit dose" for the purpose of the present invention means a physically determined unit which contains an individual amount of the active ingredient in combination with a pharmaceutical excipient, the content of active compound in the unit dose corresponding to a fraction or multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain about 2 to 200 mg, advantageously 10 to 100 mg and in particular 20 to 60 mg, of active compound.

In general, it has proved advantageous in human medicine to administer the active compound or compounds, when these are given orally, in a daily dose of about 0.1 to about 30, preferably 0.3 to 15 and in particular 0.6 to 3, mg/kg of body weight, if appropriate in the form of several, preferably 1 to 3, individual administrations in order to achieve the desired results. An individual administration contains the active compound or compounds in amounts of about 0.05 to about 10, preferably 0.1 to 5 and in particular 0.3 to 1, mg/kg of body weight.

Similar dosages can be used in the case of a parenteral treatment, for example an intravenous or intramuscular administration. About 0.3 to 1 mg of active compound/kg of body weight is administered in this therapy. As the case may be, the dose may be increased to 0.3 to 15, in case of need to 0.3 to 30 mg of active compound/kg of body weight. In the case of long-term medication, the pharmaceutical formulation is in general administered, for therapeutic purposes, at fixed points in time, such as 1 to 4 times daily, for example after each meal and/or in the evening. In acute cases, medication takes place at varying points in time. Under certain circumstances, it may be necessary to deviate from the dosages mentioned, and in particular to do so in accordance with the nature, body weight and age of the individual to be treated, the nature and severity of the illness, the nature of the formulation and of the administration of the medicament, and the time or interval over which administration takes place. Thus, in some cases it can suffice to manage with less than the abovementioned amount of active compound, while in other cases it is necessary to exceed the amount of active compound mentioned above. The optimum dosage and method of administration of the active compounds required in each particular case can be determined by the expert in accordance with his expert knowledge.

The pharmaceutical formulations as a rule consist of the active compounds according to the invention and non-toxic, pharmaceutically acceptable medicinal excipients, which are used as an admixture or diluent in solid, semi-solid or liquid form, or as a means of encasing, for example in the form of a capsule, a tablet coating, a sachet or some other container for the therapeutically active ingredient. An excipient can, for example, serve as a promoter of the absorption of the medicament by the body, as a formulating auxiliary, as a sweetener, as a flavour correctant, as a colorant or as a preservative.

Examples of forms which may be used orally are tablets, dragees, hard and soft capsules, for example capsules made of gelatine, dispersible powders, granules, aqueous and oily suspensions, emulsions or solutions.

Tablets may contain inert diluents, for example calcium carbonate, calcium phosphate, sodium phosphate or xylitol; granulating agents and dispersing agents, for example calcium phosphate or alginates; binders, for example starch, gelatine or gum acacia; and lubricants, for example aluminium stearate or magnesium stearate, talc or silicone oil. The tablets may additionally be provided with a coating, which can also be such that delayed dissolution and resorption of the medicament in the gastro-intestinal tract and hence, for example, better toleration, a protracted effect or a retarded effect are achieved. Gelatine capsules may contain the medicament mixed with a solid diluent, for example calcium carbonate or kaolin, or an oily diluent, for example paraffin oil.

Aqueous suspensions may contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitol monooleate, polyoxyethylene sorbitan monooleate or lecithin; preservatives, for example methyl hydroxybenzoate or propyl hydroxybenzoate; flavouring agents; and sweeteners, for example saccharin or sodium cyclamate.

Oily suspensions may contain, for example, paraffin oil and thickeners, such as beeswax, hard paraffin or cetyl alcohol; and furthermore sweeteners, flavouring agents and antioxidants.

Water-dispersible powders and granules may contain the medicaments mixed with dispersing agents, wetting agents and suspending agents, for example those mentioned above, as well as with sweeteners, flavouring agents and colorants.

Emulsions may contain, for example, paraffin oil, in addition to emulsifying agents, such as gum acacia, gum tragacanth, phosphatides, sorbitan monooleate or polyoxyethylene sorbitan monooleate, and sweeteners and flavouring agents.

For parenteral administration of the medicaments, sterile injectable aqueous suspensions, for example isotonic salt solutions or other solutions which can contain dispersing agents or wetting agents and/or pharmacologically acceptable diluents, for example propylene glycol or butylene glycol, are used.

The active compound or compounds can also be formulated in a micro-encapsulated form, if appropriate together with one or more of the excipients or additives indicated.

In addition to the epoxycycloalkylalkanecarboxylic acids according to the invention, in which the substituents have the meaning indicated above, and/or their salts, the pharmaceutical formulations can also contain one or more pharmacologically active ingredients from other groups of medicaments, such as antidiabetics (sulphonamides, sulphonylureas and others), for example carbutamide, tolbutamide, chlorpropamide, glibenclamide, glibornuride, glisoxepide, gliquidone or glymidine, or hypolipidaemics, such as nicotinic acid and its derivatives and salts.

The invention further relates to a process for the preparation of epoxycycloalkylalkanecarboxylic acids of the general formula I

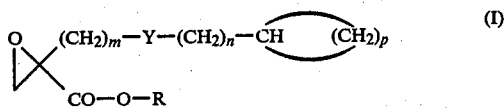
(I)

wherein R denotes a hydrogen atom or a lower alkyl group, Y denotes an oxygen atom (—O—) or a methylene group (—CH$_2$—), m denotes an integer from 0 to 6, n denotes an integer from 0 to 6 and p denotes an integer from 2 to 11 (and m cannot be 0 or 1 if Y is an oxygen atom, and the sum of the numbers m, n and p is an integer from 6 to 15), and also the salts of the carboxylic acids, which is characterised in that a substituted α-methylenecarboxylic acid of the general formula II

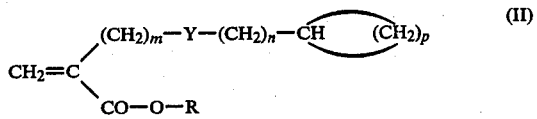
(II)

wherein R, Y, m, n and p have the meanings indicated above, is oxidised and, if appropriate, the resulting lower alkyl esters are then saponified and, if desired, subsequently converted into the salts or the resulting acids are converted into the salts or lower alkyl esters.

The oxidation of the α-methylenecarboxylic acids II is effected under conditions such as are known to the expert for the oxidation of carbon-carbon double bonds to give epoxides. Examples of suitable oxidising agents are peroxo compounds, such as hydrogen peroxide, peracetic acid, trifluoroperacetic acid, 3,5-dinitroperbenzoic acid or preferably m-chloroperbenzoic acid or permaleic acid. The reaction is expediently carried out in inert solvents, for example aromatic or chlorinated hydrocarbons, such as benzene, toluene, methylene dichloride or chloroform. The reaction temperatures are between 0° and the boiling point of the solvent, preferably between 20° and 70° C.

The saponification of the lower alkyl esters is effected in a manner which is in itself known. It is carried out at room temperature, for example using an aqueous or alcoholic (for example ethanolic) alkali metal hydroxide (for example potassium hydroxide) solution, if appropriate with the addition of an inert diluent, such as dioxan, tetrahydrofuran or toluene.

The conversion of the acids of the general formula I (R=—H) and/or of the embodiments I* and I** into the salts can be effected by direct alkaline hydrolysis of the acid derivatives I (R=lower alkyl). The alkaline reactant used is the inorganic or organic base forming the salt which is desired. However, the salts are also obtained by reacting the acids I (R=—H) with the stoichiometric equivalent of a suitable base, for example sodium hydroxide or sodium ethylate, or readily soluble salts are converted by double decomposition into sparingly soluble salts, or any desired salts are converted into pharmacologically acceptable salts.

The conversion of the carboxylic acids of the general formula I (R=—H) and/or of the embodiments I* and I** into the lower alkyl esters (R=lower alkyl) is effected in a conventional manner. For example, they are esterified with lower alkanols in the presence of strong acids, such as sulphuric acid or p-toluenesulphonic acid, or acid ion exchangers under conditions in which decarboxylation does not take place, or are esterified with dialkyl sulphates or alkyl halides in the presence of diazabicycloundecene or diazabicyclononene in inert solvents, such as benzene, toluene or acetone.

The compounds of the general formula I are normally produced in the form of racemic mixtures which are separated into the enantiomers by means of known processes. For example, the racemate is converted by means of an optically active resolving agent into diastereomers which are subsequently separated by selective crystallisation and are converted into the corresponding optical isomers. Examples of optically active resolving agents used are optically active bases, such as 1-1-phenylethylamine, d-1-phenylethylamine, cinchonidine or d-ephedrine, from which salts of the acids of the general formula I are prepared, or optically active alcohols, such as borneol or menthol, from which esters of the acids of the general formula I are prepared. It is also possible to resolve racemic mixtures into the optical isomers by chromatography on optically active adsorbents. Alternatively, the α-methylenecarboxylic acids II are first reacted with an optically active resolving agent, for example borneol or menthol, and the resulting products are oxidised to give the corresponding mixtures of diastereomers of the carboxylic acid esters, from which the optical isomers of the acids I are then obtained in a conventional manner.

α-Methylenecarboxylic acids of the general formulae II* and II**

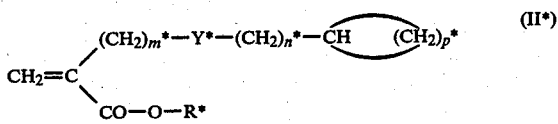
(II*)

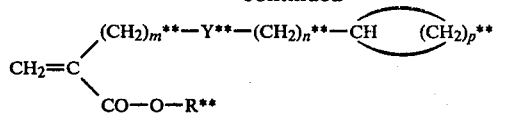

wherein R*, Y*, m*, n* and p* and R, Y, m, n and p**, respectively, have the meaning indicated above, are employed in order to prepare the epoxycycloalkylalkanecarboxylic acids of the embodiments I* and I**.

The α-methylenecarboxylic acids of the general formulae II, II* and II** can be prepared by methods which are in themselves known. They are valuable intermediate products for the synthesis of the carboxylic acids, I, I* and I**.

The preparation of the α-methylenecarboxylic acids II is effected, for example, analogously to the method of H. Stetter and H. Kuhlmann [Synthesis 1979, 29] by reacting malonic acid half-esters of the general formula III

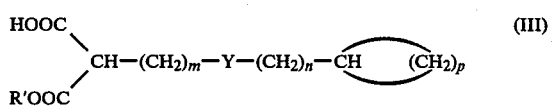

wherein Y, m, n and p have the meaning indicated above and R' denotes a lower alkyl group, with formaldehyde in pyridine in the presence of secondary amines, preferably piperidine, and, if appropriate, subsequently saponifying the resulting lower alkyl esters.

The preparation of the malonic acid half-esters III is effected by methods such as are familiar to the expert, for example by reacting dialkyl malonates IV with cycloalkylalkyl compounds V and partially saponifying the resulting malonic acid diesters VI in accordance with the following reaction scheme

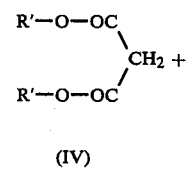

(IV)

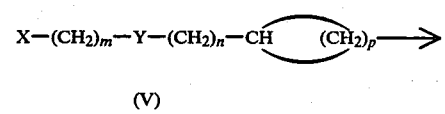

(V)

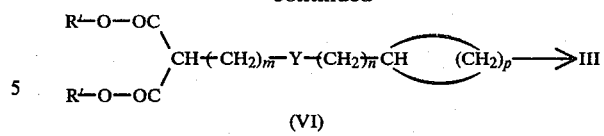

wherein R', Y, m, n and p have the meaning indicated above and X denotes a leaving group, for example a chlorine or bromine atom or a mesyloxy or p-toluenesulphonyloxy group.

Correspondingly substituted starting compounds III* or III**, IV* or IV**, V* or V**, respectively, in which the substituents Y*, m*, n* and p* or Y, m, n and p, respectively, have the meanings indicated above, R'* denotes a lower alkyl group, R'** denotes a methyl or ethyl group and X* or X** denotes a chlorine or bromine atom or a mesyloxy or p-toluenesulphonyloxy group, are employed for the preparation of the α-methylenecarboxylic acids II* or II**.

The cycloalkylalkyl compounds V and their embodiments V* and V** are known compounds or are prepared in accordance with known processes.

For example, compounds V in which Y represents a methylene group (—CH$_2$—), can be prepared from known starting compounds by conventional chain lengthening reactions. Thus, for example, cycloalkylalkyl compounds V of any desired chain length can be prepared starting from cycloalkyl halides, by reacting the latter with alkali metal cyanides or by a Grignard reaction with carbon dioxide or ethylene oxide, converting the product formed into the corresponding cycloalkylalkyl halogen compound and subsequently lengthening the chain further, if necessary carrying out this reaction several times (for example a malonic ester synthesis with subsequent decarboxylation, reduction and conversion of the alcohol formed into the halogen compound).

Compounds V in which Y represents an oxygen atom (—O—), can be prepared in various ways, for example in accordance with the following reaction scheme

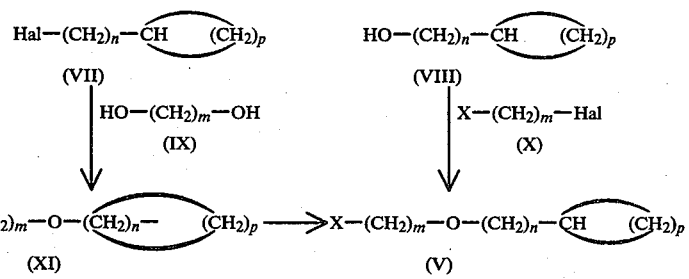

wherein n, p and X have the meanings indicated above, Hal represents a halogen atom and m represents an integer from 2 to 6 [in this connection see also J. Augstein et al. (J.Med.Chem. 8 (1965) 356–367), J. D. Genzer et al. (J.Amer.Chem.Soc. 73 (1951) 3,159–3,162) and Sh. Mamedov et al., (Zh.Obshch.Khim. 32, 799 (1962), 33, 3,166 (1963)].

The cycloalkyl compounds VII and VIII are known or are prepared (as described above) in a known manner, for example by chain lengthening.

For the reaction with the halogen compounds VII or X, the alcohols VIII or the diols IX are preferably converted into the (mono)alcoholates. The conversion of the alcohols XI into the compounds V in which X represents, for example, a chlorine atom is effected, for example, by reaction with thionyl chloride.

The examples which follow serve to illustrate the invention without limiting it. Bp denotes boiling point and mp denotes melting point. Temperature data are quoted in °C.

EXAMPLES

Example 1

2-(3-Cyclohexylpropyl)-oxirane-2-carboxylic acid ethyl ester (a) 2-(3-Cyclohexylpropyl)-oxirane-2-carboxylic acid ethyl ester 7.9 g of 5-cyclohexyl-2-methylenevaleric acid ethyl ester and 12.2 g of m-chloroperbenzoic acid in 100 ml of methylene chloride are boiled under reflux for 21 hours. The mixture is cooled to 0° C., the precipitate is filtered off and washed with 50 ml of methylene chloride and the combined filtrates are concentrated. The turbid, oily residue is dissolved in 60 ml of acetone and dilute sodium carbonate solution is added, while cooling with ice, until a pH value of 9 is reached. 100 ml of water are also added and the mixture is extracted with 3 times 100 ml of diethyl ether. The combined organic phases are dried over sodium sulphate and concentrated and the oily residue is distilled. This gives 4.9 g of the title compound, bp 100°–108° C. at 0.02 mm Hg (2.7 Pa).

(b) 5-Cyclohexyl-2-methylenevaleric acid ethyl ester 51 g of (3-cyclohexylpropyl)-malonic acid ethyl ester, 6.4 g of paraformaldehyde, 50 ml of pyridine and 2.1 g of piperidine are warmed to 60° C. When the evolution of carbon dioxide is complete (approx. 1 hour), the mixture is stirred for a further hour at 60° C. and is poured into 800 ml of water and the mixture is extracted with 4 times 200 ml of petroleum ether. The combined organic phases are washed with 200 ml of water, 200 ml of 2 N hydrochloric acid, 200 ml of water and 200 ml of saturated sodium bicarbonate solution and are dried over sodium sulphate and concentrated. The residue is purified by chromatography on a silica gel column. (Migrating agent 80:20 petroleum ether/ethyl acetate). This gives 36.7 g of 5-cyclohexyl-2-methylenevaleric acid ethyl ester in the form of a nearly colourless oil.

(c) (3-Cyclohexylpropyl)-malonic acid ethyl ester

A solution of 13.5 g of potassium hydroxide in 160 ml of ethanol is added dropwise in the course of one hour and while stirring to 68 g of (3-cyclohexylpropyl)-malonic acid diethyl ester (prepared analogously to Example 4d), dissolved in 160 ml of ethanol. After stirring for 24 hours at room temperature, the mixture is concentrated considerably in vacuo and the residue is dissolved in 400 ml of water and extracted with 300 ml of diethyl ether. 40 ml of half-concentrated hydrochloric acid are added to the aqueous phase, while cooling with ice, and the mixture is extracted with 3 times 300 ml of diethyl ether. The combined organic phases are dried over sodium sulphate and concentrated. This gives 51 g of (3-cyclohexylpropyl)-malonic acid ethyl ester in the form of a viscous, yellowish oil.

Example 2

2-(4-Cyclohexylbutyl)-oxirane-2-carboxylic acid ethyl ester (a) 2-(4-Cyclohexylbutyl)-oxirane-2-carboxylic acid ethyl ester 3.8 g of the title compound are obtained in the form of a colourless oil, bp 110°–118° C. at 0.01 mm Hg (1.3 Pa) by the procedure described in Example 1a) from 6.4 g of 6-cyclohexyl-2-methylenehexanoic acid ethyl ester and 9.3 g of m-chloroperbenzoic acid in 80 ml of methylene chloride.

(b) 6-Cyclohexyl-2-methylenehexanoic acid ethyl ester 16.6 g of 6-cyclohexyl-2-methylenehexanoic acid ethyl ester, in the form of a nearly colourless oil, which is purified by chromatography on silica gel (migrating agent: 80:20 petroleum ether/ethyl acetate), are obtained by the procedure described in Example (1b) from 26 g of (4-cyclohexylbutyl)-malonic acid ethyl ester, 3.1 g of paraformaldehyde, 19 ml of pyridine and 1.2 ml of piperidine.

(c) (4-Cyclohexylbutyl)-malonic acid ethyl ester 26.1 g of (4-cyclohexylbutyl)-malonic acid ethyl ester are obtained in the form of a viscous, yellowish oil by the procedure described in Example (1c) from 35 g of (4-cyclohexylbutyl)-malonic acid diethyl ester (prepared analogously to Example 4d) and 6.7 g of potassium hydroxide in 150 ml of ethanol.

Example 3

2-(5-Cyclohexylpentyl)-oxirane-2-carboxylic acid ethyl ester (a) 2-(5-Cyclohexylpentyl)-oxirane-2-carboxylic acid ethyl ester 5.3 g of the title compound, bp 115°–123° C. at 0.005 mm Hg (0.7 Pa), are obtained by the procedure described in Example (1a) from 9.9 g of 7-cyclohexyl-2-methyleneheptanoic acid ethyl ester and 13.6 g of m-chloroperbenzoic acid in 100 ml of methylene chloride.

(b) 7-Cyclohexyl-2-methyleneheptanoic acid ethyl ester 23.6 g of 7-cyclohexyl-2-methyleneheptanoic acid ethyl ester are obtained in the form of a colourless oil by the procedure described in Example (1b) from 35.5 g of (5-cyclohexylpentyl)-malonic acid ethyl ester, 4.0 g of paraformaldehyde, 25 ml of pyridine and 1.5 ml of piperidine. (Migrating agent 1:1 petroleum ether/methylene chloride).

(c) (5-Cyclohexylpentyl)-malonic acid ethyl ester 35.5 g of (5-cyclohexylpentyl)-malonic acid ethyl ester are obtained in the form of a viscous, yellowish oil by the procedure described in Example (1c) from 47.2 g of (5-cyclohexylpentyl)-malonic acid diethyl ester (prepared analogously to Example 4d) and 8.6 g of potassium hydroxide in 200 ml of ethanol.

Example 4

2-[4-(Cyclohexyloxy)-butyl]-oxirane-2-carboxylic acid ethyl ester (a) 2-[4-(Cyclohexyloxy)-butyl]-oxirane-2-carboxylic acid ethyl ester 2.4 g of the title compound, in the form of a colourless oil, which is purified by chromatography on silica gel (migrating agent: 90:10 petroleum ether/ethyl acetate), are obtained by the procedure described in Example 1a) from 4.9 g of 6-cyclohexyloxy-2-methylenehexanoic acid ethyl ester and 7 g of m-chloroperbenzoic acid in 50 ml of methylene chloride.

(b) 6-Cyclohexyloxy-2-methylenehexanoic acid ethyl ester 4.9 g of 6-cyclohexyloxy-2-methylenehexanoic acid ethyl ester, in the form of a colourless oil, which is purified by chromatography on silica gel (migrating agent: 90:10 petroleum ether/ethyl acetate), are obtained by the procedure described in Example (1b) from 7.4 g of [4-(cyclohexyloxy)-butyl]-malonic acid ethyl ester, 0.85 g of paraformaldehyde, 5.2 ml of pyridine and 0.3 ml of piperidine.

(c) [4-(Cyclohexyloxy)-butyl]-malonic acid ethyl ester 7.4 g of [4-(cyclohexyloxy)-butyl]-malonic acid ethyl ester are obtained by the procedure described in Example (1c) from 10.5 g of [4-(cyclohexyloxy)-butyl]-malonic acid diethyl ester and 1.9 g of potassium hydroxide in 50 ml of ethanol.

(d) [4-(Cyclohexyloxy)-butyl]-malonic acid diethyl ester 15 g of malonic acid diethyl ester are added dropwise at 50° C. to a solution of sodium ethylate, freshly prepared from 1.5 g of sodium and 30 ml of ethanol. This temperature is maintained for 1 hour and 11.7 g of 4-cyclohexyloxybutyl bromide are then added dropwise. When the addition is complete, the mixture is stirred for 3 hours at 60° C. and is concentrated considerably, 100 ml of ice water are added to the residue and the mixture is extracted 3 times with a total of 150 ml of methylene chloride. The combined organic phases are dried over sodium sulphate and the solvent is removed by distillation in vacuo, together with excess malonic acid diethyl ester. This gives 10.5 g of [4-(cyclohexyloxy)-butyl]-malonic acid diethyl ester in the form of a pale yellow oily residue.

Example 5

2-[4-(2-Cyclohexylethoxy)-butyl]-oxirane-2-carboxylic acid ethyl ester (a) 2-[4-(2-Cyclohexylethoxy)-butyl]-oxirane-2-carboxylic acid ethyl ester 5.3 g of the title compound, in the form of an oil, which is purified by chromatography on silica gel (migrating agent: 9:1 petroleum ether/ethyl acetate), are obtained by the procedure described in Example (1a) from 11.2 g of 6-(2-cyclohexylethoxy)-2-methylenehexanoic acid ethyl ester and 13.7 g of m-chloroperbenzoic acid in 100 ml of methylene chloride.

(b) 6-(2-Cyclohexylethoxy)-2-methylenehexanoic acid ethyl ester 11.2 g of 6-(2-cyclohexylethoxy)-2-methylenehexanoic acid ethyl ester, in the form of a nearly colourless oil, which is purified by chromatography on silica gel (migrating agent: 9:1 petroleum ether/ethyl acetate), are obtained by the procedure described in Example 1b from 16.5 g of [4-(2-cyclohexylethoxy)-butyl]-malonic acid ethyl ester, 1.97 g of paraformaldehyde, 12 ml of pyridine and 0.7 ml of piperidine.

(c) [4-(2-Cyclohexylethoxy)-butyl]-malonic acid ethyl ester 16.5 g of [4-(2-cyclohexylethoxy)-butyl]-malonic acid ethyl ester are obtained in the form of a thick, yellow oil by the procedure described in Example (1c) from 22 g of [4-(2-cyclohexylethoxy)-butyl]-malonic acid diethyl ester and 3.6 g of potassium hydroxide in 150 ml of ethanol.

(d) [4-(2-Cyclohexylethoxy)-butyl]-malonic acid diethyl ester 22 g of [4-(2-cyclohexylethoxy)-butyl]-malonic acid diethyl ester are obtained in the form of a yellow oil by the procedure described in Example (4d) from 27.7 g of 4-(2-cyclohexylethoxy)-butyl bromide, 25.3 g of malonic acid diethyl ester and a solution of 2.9 g of sodium in 150 ml of ethanol.

Example 6

2-(7-Cyclohexylheptyl)-oxirane-2-carboxylic acid ethyl ester (a) 2-(7-Cyclohexylheptyl)-oxirane-2-carboxylic acid ethyl ester 5.25 g of the title compound, in the form of a colourless oil, which is purified by chromatography on silica gel (migrating agent: 90:10 petroleum ether/ethyl acetate), are obtained by the procedure described in Example (1a) from 9.2 g of 9-cyclohexyl-2-methylenenonanoic acid ethyl ester and 11.3 g of m-chloroperbenzoic acid in 100 ml of methylene chloride.

(b) 9-Cyclohexyl-2-methylenenonanoic acid ethyl ester 9.2 g of 9-cyclohexyl-2-methylenenonanoic acid ethyl ester, in the form of a colourless oil, which is purified by chromatography on silica gel (migrating agent: 95:5 petroleum ether/ethyl acetate), are obtained by the procedure described in Example (1b) from 16.2 g of (7-cyclohexylheptyl)-malonic acid ethyl ester, 1.86 g of paraformaldehyde, 11.5 ml of pyridine and 0.6 ml of piperidine.

(c) (7-Cyclohexylheptyl)-malonic acid ethyl ester 16.3 g of (7-cyclohexylheptyl)-malonic acid ethyl ester are obtained in the form of a yellow, thick oil by the procedure described in Example (1c) from 21.6 g of (7-cyclohexylheptyl)-malonic acid diethyl ester (prepared analogously to Example 4d) and 3.55 g of potassium hydroxide in 150 ml of ethanol.

Example 7

2-(6-Cyclopropylhexyl)-oxirane-2-carboxylic acid ethyl ester (a) 2-(6-Cyclopropylhexyl)-oxirane-2-carboxylic acid ethyl ester 1.18 g of the title compound, in the form of a yellowish oil, which is purified by chromatography on silica gel (migrating agent: 90:10 petroleum ether/ethyl acetate), are obtained by the procedure described in Example (1a) from 2.5 g of 8-cyclopropyl-2-methyleneoctanoic acid ethyl ester and 3.85 g of m-chloroperbenzoic acid in 30 ml of methylene chloride.

(b) 8-Cyclopropyl-2-methyleneoctanoic acid ethyl ester 2.5 g of 8-cyclopropyl-2-methyleneoctanoic acid ethyl ester, in the form of a yellowish oil, which is purified by chromatography on silica gel (migrating agent: 90:10 petroleum ether/ethyl acetate), are obtained by the procedure described in Example (1b) from 4.53 g of (6-cyclopropylhexyl)-malonic acid ethyl ester 0.64 g of paraformaldehyde, 4 ml of pyridine and 0.2 ml of piperidine.

(c) (6-Cyclopropylhexyl)-malonic acid ethyl ester 4.53 g of (6-cyclopropylhexyl)-malonic acid ethyl ester are obtained in the form of a yellow oil by the procedure described in Example (1c) from 6.4 g of (6-cyclopropylhexyl)-malonic acid diethyl ester and 1.26 g of potassium hydroxide in 40 ml of ethanol.

(d) (6-Cyclopropylhexyl)-malonic acid diethyl ester 6.4 g of (6-cyclopropylhexyl)-malonic acid diethyl ester are obtained in the form of a yellow oil by the procedure described in Example (4d) from 6.8 g of 6-cyclopropylhexyl bromide, 7.95 g of malonic acid diethyl ester and a solution of 0.91 g of sodium in 40 ml of ethanol.

Example 8

2-(3-Cyclopentylpropyl)-oxirane-2-carboxylic acid ethyl ester (a) 2-(3-Cyclopentylpropyl)-oxirane-2-carboxylic acid ethyl ester 19 g of the title compound are obtained in the form of a colourless oil, bp. 89°–93° C. at 0.04 mm Hg (5.3 Pa), by the procedure described in Example (1a) from 20 g of 5-cyclopentyl-2-methylenevaleric acid ethyl ester and 24.2 g of m-chloroperbenzoic acid in 250 ml of methylene chloride.

(b) 5-Cyclopentyl-2-methylenevaleric acid ethyl ester 20.2 g of 5-cyclopentyl-2-methylenevaleric acid ethyl ester, bp. 63°–65° C. at 0.01 mm Hg (1.3 Pa), are obtained by the procedure described in Example (1b) from 43.8 g of (3-cyclopentylpropyl)-malonic acid ethyl ester, 5.7 g of paraformaldehyde, 45 ml of pyridine and 1.55 g of piperidine.

(c) (3-Cyclopentylpropyl)-malonic acid ethyl ester 43.8 g of (3-cyclopentylpropyl)-malonic acid ethyl ester are obtained in the form of a yellow oil by the procedure described in Example (1c) from 72.8 g of (3-cyclopentylpropyl)-malonic acid diethyl ester (prepared analogously to Example 4d) and 17.7 g of potassium hydroxide in 580 ml of ethanol.

Example 9

2-(4-Cyclopentylbutyl)-oxirane-2-carboxylic acid ethyl ester (a) 2-(4-Cyclopentylbutyl)-oxirane-2-carboxylic acid ethyl ester 4.0 g of the title compound are obtained in the form of a colourless oil, bp 100°–107° C. at 0.03 mm Hg (4 Pa), by the procedure described in Example (1a) from 8.5 g of 6-cyclopentyl-2-methylenehexanoic acid ethyl ester and 13.1 g of m-chloroperbenzoic acid in 120 ml of methylene chloride.

(b) 6-Cyclopentyl-2-methylenehexanoic acid ethyl ester 8.5 g of 6-cyclopentyl-2-methylenehexanoic acid ethyl ester, bp 80°–87° C. at 0.01 mm Hg (1.3 Pa), are obtained by the procedure described in Example (1b) from 18.3 g of (4-cyclopentylbutyl)-malonic acid ethyl ester, 2.6 g of paraformaldehyde, 20 ml of pyridine and 0.9 ml of piperidine.

(c) (4-Cyclopentylbutyl)-malonic acid ethyl ester 18.3 g of (4-cyclopentylbutyl)-malonic acid ethyl ester are obtained in the form of a viscous oil by the procedure described in Example (1c) from 29.9 g of (4-cyclopentylbutyl)-malonic acid diethyl ester (prepared analogously to Example 4d) and 5.9 g of potassium hydroxide in 200 ml of ethanol.

Example 10

2-(6-Cyclopentylhexyl)-oxirane-2-carboxylic acid ethyl ester (a) 2-(6-Cyclopentylhexyl)-oxirane-2-carboxylic acid ethyl ester 5.33 g of the title compound, in the form of a nearly colourless oil, which is purified by chromatography on silica gel (migrating agent: 90:10 petroleum ether/ethyl acetate), are obtained by the procedure described in Example (1a) from 11.4 g of 8-cyclopentyl-2-methyleneoctanoic acid ethyl ester and 15.6 g of m-chloroperbenzoic acid in 120 ml of methylene chloride (b) 8-Cyclopentyl-2-methyleneoctanoic acid ethyl ester 11.5 g of 8-cyclopentyl-2-methyleneoctanoic acid ethyl ester, in the form of a nearly colourless oil, which is purified by chromatography on silica gel (migrating agent: 95:5 petroleum ether/ethyl acetate), are obtained by the procedure described in Example (1b) from 22.1 g of (6-cyclopentylhexyl)-malonic acid ethyl ester, 2.8 g of paraformaldehyde, 22 ml of pyridine and 1 ml of piperidine.

(c) (6-Cyclopentylhexyl)-malonic acid ethyl ester 22.1 g of (6-cyclopentylhexyl)-malonic acid ethyl ester are obtained in the form of a yellow oil by the procedure described in Example (1c) from 37.9 g of (6-cyclopentylhexyl)-malonic acid diethyl ester and 6.8 g of potassium hydroxide in 200 ml of ethanol.

(d) (6-Cyclopentylhexyl)-malonic acid diethyl ester 38 g of (6-cyclopentylhexyl)-malonic acid diethyl ester are obtained in the form of an oil by the procedure described in Example (4d) from 48.9 g of 6-cyclopentyl-hexyl bromide, 50.3 g of malonic acid diethyl ester and a solution of 5.8 g of sodium in 300 ml of ethanol.

Example 11

2-(3-Cycloheptylpropyl)-oxirane-2-carboxylic acid ethyl ester (a) 2-(3-Cycloheptylpropyl)-oxirane-2-carboxylic acid ethyl ester 9.3 g of the title compound, bp 107°–110° C. at 0.08 mm Hg (10.6 Pa), are obtained by the procedure described in Example (1a) from 18.2 g of 5-cycloheptyl-2-methylenevaleric acid ethyl ester and 26.3 g of m-chloroperbenzoic acid in 200 ml of methylene chloride.

(b) 5-Cycloheptyl-2-methylenevaleric acid ethyl ester 18.2 g of 5-cycloheptyl-2-methylenevaleric acid ethyl ester, bp 89°–98° C. at 0.01 mm Hg (1.3 Pa), are obtained by the procedure described in Example (1b) from 33.3 g of (3-cycloheptylpropyl)-malonic acid ethyl ester, 4.43 g of paraformaldehyde, 35 ml of pyridine and 1.6 ml of piperidine.

(c) (3-Cycloheptylpropyl)-malonic acid ethyl ester 33.3 g of (3-cycloheptylpropyl)-malonic acid ethyl ester are obtained in the form of a yellow oil by the procedure described in Example (1c) from 49.7 g of (3-cycloheptylpropyl)-malonic acid diethyl ester and 9.33 g of potassium hydroxide in 300 ml of ethanol.

(d) (3-Cycloheptylpropyl)-malonic acid diethyl ester 49.8 g of (3-cycloheptylpropyl)-malonic acid diethyl ester, bp 120°–122° C. at 0.08 mm Hg (10.6 Pa), are obtained by the procedure described in Example (4d) from 63 g of 3-cycloheptylpropyl bromide, 69 g of malonic acid diethyl ester and a solution of 7.9 g of sodium in 400 ml of ethanol.

Example 12

2-(3-Cyclooctylpropyl)-oxirane-2-carboxylic acid ethyl ester (a) 2-(3-Cyclooctylpropyl)-oxirane-2-carboxylic acid ethyl ester 2.2 g of the title compound, in the form of a colourless oil, which is purified by chromatography on silica gel (migrating agent: 90:10 petroleum ether/ethyl acetate), are obtained by the procedure described in Example (1a) from 5.42 g of 5-cyclooctyl-2-methylenevaleric acid ethyl ester and 5.55 g of m-chloroperbenzoic acid in 50 ml of methylene chloride.

(b) 5-Cyclooctyl-2-methylenevaleric acid ethyl ester 5.5 g of 5-cyclooctyl-2-methylenevaleric acid ethyl ester, in the form of an oil, which is purified by chromatography on silica gel (migrating agent: 95:5 petroleum ether/ethyl acetate), are obtained by the procedure described in Example (1b) from 10.1 g of (3-cyclooctylpropyl)-malonic acid ethyl ester, 1.28 g of paraformaldehyde, 10 ml of pyridine and 0.5 ml of piperidine.

(c) (3-Cyclooctylpropyl)-malonic acid ethyl ester 10.2 g of (3-cyclooctylpropyl)-malonic acid ethyl ester are obtained in the form of a yellowish oil by the procedure described in Example (1c) from 16 g of (3-cyclooctylpropyl)-malonic acid diethyl ester and 2.87 g of potassium hydroxide.

(d) (3-Cyclooctylpropyl)-malonic acid diethyl ester 16 g of (3-cyclooctylpropyl)-malonic acid diethyl ester are obtained in the form of a yellowish oil by the procedure described in Example (4d) from 20.0 g of 3-cyclooctylpropyl bromide, 20.6 g of malonic acid diethyl ester and a solution of 2.37 g of sodium in 180 ml of ethanol.

(e) 3-Cyclooctylpropyl bromide 19.7 g of 2-cyclooctyl-propan-1-ol are boiled under reflux for 3 hours with 35 ml of 48% strength hydrobromic acid and 0.1 g of red phosphorus, 7 ml of concentrated sulphuric acid are added and the mixture is boiled for a further 3 hours. It is poured into 100 ml of ice water and the mixture is extracted with twice 100 ml of diethyl ether and the combined organic phases are dried over sodium sulphate and concentrated. 20.0 g of 3-cyclooctylpropyl bromide are left as residue in the form of a brown oil.

Example 13

2-(3-Cycloundecylpropyl)-oxirane-2-carboxylic acid ethyl ester (a) 2-(3-Cycloundecylpropyl)-oxirane-2-carboxylic acid ethyl ester 2.2 g of the title compound, in the form of a colourless oil, which is purified by chromatography on silica gel (migrating agent: 90:10 petroleum ether/ethyl acetate; thin layer chromatography on silica gel with petroleum ether/ethyl acetate 9:1:$R_f$=0.5), are obtained by the procedure described in Example (1a) from 4.4 g of 5-cycloundecyl-2-methylenevaleric acid ethyl ester and 5.15 g of m-chloroperbenzoic acid in 40 ml of methylene chloride.

(b) 5-Cycloundecyl-2-methylenevaleric acid ethyl ester 4.4 g of 5-cycloundecyl-2-methylenevaleric acid ethyl ester, in the form of a yellowish oil, which is purified by chromatography on silica gel (migrating agent: 95:5 petroleum ether/ethyl acetate), are obtained by the procedure described in Example (1b) from 7.6 g of (3-cycloundecylpropyl)-malonic acid ethyl ester, 0.84 g of paraformaldehyde, 7 ml of pyridine and 0.3 ml of piperidine.

(c) (3-Cycloundecylpropyl)-malonic acid ethyl ester 7.6 g of (3-cycloundecylpropyl)-malonic acid ethyl ester are obtained in the form of a thick, yellow oil by the procedure described in Example (1c) from 10.6 g of (3-cycloundecylpropyl)-malonic acid diethyl ester and 1.67 g of potassium hydroxide in 40 ml of ethanol.

(d) (3-Cycloundecylopropyl)-malonic acid diethyl ester 10.6 g of (3-cycloundecylpropyl)-malonic acid diethyl ester are obtained in the form of an oil by the procedure described in Example (4d) from 15 g of 3-cycloundecylpropyl bromide, 13 g of malonic acid diethyl ester and a solution of 1.5 g of sodium in 80 ml of ethanol.

(e) 3-Cycloundecylpropyl bromide 15 g of 3-cycloundecylpropyl bromide are obtained in the form of an oil by the procedure described in Example (12e) from 16 g of 3-cycloundecylpropan-1-ol, 30 ml of 48% strength hydrobromic acid, 0.1 g of red phosphorus and 5 ml of concentrated sulphuric acid.

The starting material 3-cycloundecylpropan-1-ol is obtained as follows: hydroxymethylcycloundecane is reacted with thionyl chloride to give chloromethylcycloundecane, which is reacted with malonic acid diethyl ester in the presence of sodium ethylate to give (cycloundecylmethyl)-malonic acid diethyl ester, which, after saponifying the ester group and decarboxylating the corresponding malonic acid, gives 3-cycloundecylpropionic acid. 3-Cycloundecylpropionic acid is reduced with lithium aluminum hydride in tetrahydrofuran to give 3-cycloundecylpropanol.

Example 14

Sodium 2-(3-cyclohexylpropyl)-oxirane-2-carboxylate 1.1 g of 2-(3-cyclohexylpropyl)-oxirane-2-carboxylic acid ethyl ester are stirred for 2 hours at room temperature with 4.58 ml of 1 N sodium hydroxide solution and 5 ml of tetrahydrofuran. The mixture is concentrated to half its volume and the crystals of the title compound which have been precipitated are filtered off. Mp 105°–110° C.

Example 15

2-[2-(3-Cyclohexylpropyloxy)-ethyl]-oxirane-2-carboxylic acid ethyl ester (a) 2-[2-(3-Cyclohexylpropyloxy)-ethyl]-oxirane-carboxylic acid ethyl ester 6.8 g of the title compound, in the form of a colourless oil, which is purified by chromatography on silica gel (migrating agent: 90:10 petroleum ether/ethyl acetate) are obtained by the procedure described in Example (1a) from 12.4 g of 4-(3-cyclohexylpropyloxy)-2-methylenebutyric acid ethyl ester and 18.7 g of m-chloroperbenzoic acid in 250 ml of methylene chloride. Thin layer chromatography on silica gel with petroleum ether/ethyl acetate/glacial acetic acid 80:20:3: $R_f$=0.65.

(b) 4-(3-cyclohexylpropyloxy)-2-methylenebutyric acid ethyl ester 82.3 g of 4-(3-cyclohexylpropyloxy)-2-methylenebutyric acid ethyl ester, in the form of a colourless oil, which is purified by chromatography on silica gel (migrating agent: chloroform), are obtained by the procedure described in Example (1b) from 103.6 g of 2-(3-cyclohexylpropyloxy)-ethylmalonic acid ethyl ester, 11 g of paraformaldehyde, 105 ml of pyridine and 2.9 g of piperidine.

(c) 2-(3-Cyclohexylpropyloxy)-ethylmalonic acid ethyl ester 104.6 g of 2-(3-cyclohexylpropyloxy)-ethylmalonic acid ethyl ester are obtained in the form of a yellowish oil by the procedure described in Example (1c) from 125.4 g of 2-(3-cyclohexylpropyloxy)-ethylmalonic acid diethyl ester and 24.5 g of potassium hydroxide in 750 ml of ethanol.

(d) 2-(3-Cyclohexylpropyloxy)-ethylmalonic acid diethyl ester 125.9 g of 2-(3-cyclohexylpropyloxy)-ethylmalonic acid diethyl ester, in the form of a colourless oil [bp 138°–140° C. at 0.03 mm Hg (4.0 Pa)] are obtained by the procedure described in Example (4d) from 118.6 g of 2-(3-cyclohexylpropyloxy)-ethyl chloride, 97.4 g of malonic acid diethyl ester and a solution of 13.3 g sodium and 0.5 g of potassium iodide in 420 ml of ethanol.
(e) 2-(3-Cyclohexylpropyloxy)-ethyl chloride 110.4 g of 2-(3-cyclohexylpropyloxy)-ethanol, 2 ml of pyridine and 112 ml of thionyl chloride are boiled under reflux for 30 minutes. The reaction mixture is allowed to cool and is then poured onto 500 g of ice. The mixture is extracted with twice 500 ml of methylene chloride. The combined organic phases are washed with water, with sodium hydrogen carbonate solution, with water again and are then concentrated. The residue is distilled. 119.6 g of 2-(3-cyclohexylpropyloxy)-ethyl chloride are obtained [bp 68°–69° C. at 0.01 mm Hg (1.3 Pa)].
(f) 2-(3-Cyclohexylropyloxy)-ethanol 85 ml of xylene are added to a solution of 15.75 g of sodium in 182.2 g of ethylene glycol. The mixture is heated to 100° C., and a solution of 140.5 g of 3-cyclohexylpropyl bromide in 70 ml of xylene is added dropwise within 3 hours. When the addition has ended, the mixture is boiled for 4 hours under reflux, cooled, and then 500 ml of water are added. The mixture is extracted with twice 500 ml of petroleum ether, the combined organic phases are dried over sodium sulphate and the remaining oil is purified by chromatography on silica gel (migrating agent: 80:20 petroleum ether/ethyl acetate). 105.3 g of 2-(3-cyclohexylpropyloxy)-ethanol are obtained.

Example 16

2-(5-Cycloheptylpentyl)-oxirane-2-carboxylic acid ethyl ester (a) 2-(5-Cycloheptylpentyl)-oxirane-2-carboxylic acid ethyl ester 7.5 g of the title compound, in the form of a colourless oil, which is purified by chromatography on silica gel (migrating agent: 90:10 petroleum ether/ethyl acetate; thin layer chromatography on silica gel with petroleum ether/ethyl acetate 8:2: $R_f=0.55$), are obtained by the procedure described in Example (1a) from 13.1 g of 7-cycloheptyl-2-methyleneheptanoic acid ethyl ester and 12.0 g of m-chloroperbenzoic acid in 200 ml of methylene chloride.

(b) 7-Cycloheptyl-2-methyleneheptanoic acid ethyl ester 23.7 g of 7-cycloheptyl-2-methyleneheptanoic acid ethyl ester, in the form of a colourless oil, purified by chromatography on silica gel (migrating agent: 90:10 petroleum ether/ethyl acetate), are obtained by the procedure described in Example (1b) from 35 g of 5-cycloheptylpentylmalonic acid ethyl ester, 3,8 g of paraformaldehyde, 35 ml of pyridine and 1 g of piperidine.

(c) 5-Cycloheptylpentylmalonic acid ethyl ester 35.8 g of 5-cycloheptylpentylmalonic acid ethyl ester are obtained in the form of a tough oil by the procedure described in Example (1c) from 55.7 g of 5-cycloheptylpentylmalonic acid diethyl ester and 11.3 g of potassium hydroxide in 220 ml of ethanol.

(d) 5-Cycloheptylpentylmalonic acid diethyl ester 55.7 g of the title compound are obtained in the form of a nearly colourless oil by the procedure described in Example (4d) from 44.8 g of 5-cycloheptylpentyl bromide, 32 g of malonic acid diethyl ester and a solution of 4.2 g of sodium in 140 ml of ethanol.

(e) 5-Cycloheptylpentyl bromide 44.9 g of 5-cycloheptylpentyl bromide are obtained in the form of a light yellow oil [bp 135°–138° C. at 12 mm Hg (1600 Pa)] by the procedure described in Example (12e) from 35.3 g of 5-cycloheptylpentan-1-ol, 57 ml of 48% strength hydrobromic acid, 0.2 g of red phosphorus and 12 ml of concentrated sulphuric acid.

The starting material 5-cycloheptylpentan-1-ol is obtained as follows: cycloheptylpropylmalonic acid ethyl ester is heated to 180° C. for one hour. The resulting 5-cycloheptylvaleric acid ethyl ester [bp 80°–82° C. at 0.008 mm Hg (1.0 Pa)] is reduced with lithium aluminum hydride in tetrahydrofuran to yield 5-cycloheptylpentan-1-ol [bp 92°–94° C. at 0.008 mm Hg (1.0 Pa)].

Example 17

Sodium 2-(5-Cyclohexylpentyl)-oxirane-2-carboxylate 1.5 g of 2-(5-cyclohexylpentyl)-oxirane-2-carboxylic acid ethyl ester are stirred for 2 hours at room temperature with 5,6 ml of 1 N sodium hydroxide solution and 5 ml of tetrahydrofuran. The mixture is concentrated to half its volume and the fatty gleaming plates of the title compound which have been precipitated are filtered off.

GALENICAL EXAMPLES

Example 1

Mixture for Ampoules 100 g of sodium 2-(5-cyclohexylpentyl)-oxirane-2-carboxylate are dissolved in approx. 8 liters of twice-distilled water with the addition of an equivalent amount of sodium hydroxide solution. The pH of the solution is adjusted to 7.0±0.5 and the solution is made up to 10 liters with twice-distilled water. It is then filtered under sterile conditions and filled into 2 ml ampoules under aseptic conditions.

Example 2

10,000 capsules each containing 30 mg of active compound are prepared from the following ingredients: 300 g of 2-[2-(3-cyclohexylpropyloxy)-ethyl]-oxirane-2-carboxylic acid ethyl ester are mixed with 500 g of neutral oil and the mixture is filled into soft gelatine capsules.

Example 3

Tablets containing 25 mg of active compound are prepared as follows: 1.0 kg of sodium 2-(3-cyclohexylpropyl)-oxirane-2-carboxylate, 4.5 kg of xylitol and 3.0 kg of calcium phosphate, are granulated with 0.25 kg of polyvinylpyrrolidone (MW 25,000; MW=molecular weight) in approximately 0.5 l of water. The granules are sieved through a screen with a mesh width of 1.25 mm and, after drying, 0.9 kg of carboxymethylcellulose, 0.25 kg of talc and 0.1 kg of magnesium stearate are added. The dry granules are compressed to give tablets with a diameter of 8 mm, a weight of 250 mg and a hardness of 5–6 kg.

Pharmacology

The epoxycycloalkylalkanecarboxylic acids of formula I according to the invention lower the level of glucose and of ketones in the blood. Their chemical structure differs from that of beta-cytotropic substances (for example sulfonylureas) which have an action on the pancreas, and their mode of action differs fundamentally from that of these substances in that they have an extra-pancreatic action. They are superior to commercial preparations (for example Buformin and Phenformin) having an extra-pancreatic action.

In the following Table the investigated compounds are characterized by a serial number, which is allocated as follows:

| Serial No. | Name of Compound |
|---|---|
| 1 | Buformin |
| 2 | Phenformin |
| 3 | 2-(3-Cyclohexylpropyl)-oxirane-2-carboxylic acid ethyl ester |
| 4 | 2-(5-Cyclohexylpentyl)-oxirane-2-carboxylic acid ethyl ester |
| 5 | 2-(3-Cyclopentylpropyl)-oxirane-2-carboxylic acid ethyl ester |
| 6 | 2-(4-Cyclopentylbutyl)-oxirane-2-carboxylic acid ethyl ester |
| 7 | 2-[2-(3-Cyclohexylpropyloxy)-ethyl]-oxirane-2-carboxylic acid ethyl ester |
| 8 | 2-(3-Cycloheptylpropyl)-oxirane-2-carboxylic acid ethyl ester |
| 9 | 2-(5-Cycloheptylpentyl)-oxirane-2-carboxylic acid ethyl ester |

Table I reflects investigations of the effect of representative compounds according to the invention on the blood glucose concentration of fasting, metaboically healthy rats. Column A in each case gives the maximum lowering of the blood glucose concentration of rats which have been fasted (in %, relative to the control group) which is observed in the course of 6 hours after single oral administration of 0.6 mmole of substance/kg of body weight. Column B provides data relating to acute toxicity ($LD_{50}$; mice, peroral administration).

TABLE I

| Serial No. | A<br>Change in the blood glucose concentration (in %) in vivo | B<br>Acute toxicity $LD_{50}$(mg/kg) mice p.o. |
|---|---|---|
| 1 | −8 | 475 |
| 2 | −6 | 410* |
| 3 | −24 | 1 400 |
| 4 | −48 | 520 |
| 5 | −15 | 2 400 |
| 6 | −21 | 1 600 |
| 7 | −30 | 570 |
| 8 | −22 | 790 |
| 9 | −18 | 330 |

Re Table I:
*Cited according to Blickens, D.A.; Riggi, S.J.: Toxicol. Appl.Pharmacol., 14 (1969)393-400
Column A = maximum change in the blood glucose concentration (in %, relative to the control animals) in vivo in rats which have been fasted at a dose of 0.6 mmole/kg
Column B = Acute toxicity ($LD_{50}$ in mg/kg); mice, p.o.)

The pharmacological properties were determined by the following methods:
1. Determination of glucose in the blood after a single oral administration.

Young male Sprague-Dawley rats (body weight: 150 to 200 g) are used. The animals (6 animals per dose) are kept in Makrolon cages with up to 4 animals per cage (ambient temperature: 23° C., relative atmospheric humidity: 55%, fixed day/night rhythm [12/12 hours], standard diet: Altromin ®). The rats are deprived of the feed 18 hours before the first sample of blood is taken. Water is available ad libitum. Samples of blood are taken from the postorbital plexus by puncture immediately before and 2, 4 and 6 hours after administration of the substance.

After deproteinization with perchloric acid, the glucose in the blood is determined by means of the enzymatic HK/G-6-PDH method of R. Richterich [Klinische Chemie, Theorie und Praxis, (Clinical Chemistry, Theory and Practice), 3rd edition, 1971, S. Karger Verlag, Zurich-Basle, page 275]. A control group (10 animals, treated with pure solvent) is also investigated in each case for comparison.

2. Determination of the toxicity.

The toxicity investigations are carried out on female NMRI mice (body weight: 22 to 26 g). 18 hours before the treatment, the feed (Altromin ®) for the aniamls (5 animals per dose) is reduced to 50 g/50 animals and water is available ad libitum. Various doses of the substances (volume: 10 ml/kg) are administered orally by means of a stomach tube. The observation time is 7 days. The $LD_{50}$, that is to say the dose at which 50% of the animals die, is determined graphically from the dose/response curve.

We claim:

1. An epoxycycloalkylalkanecarboxylic acid of the formula

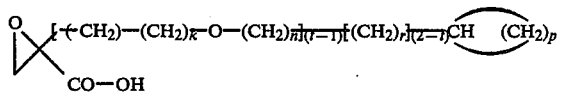

wherein
k is an integer from 1 to 5, inclusive,
n is an integer from 0 to 6, inclusive,
p is an integer from 2 to 11, inclusive,
t is a positive whole number of at most 2,
r is an integer from 1 to 13, inclusive,
a lower alkyl ester of the carboxylic acid or a salt of said carboxylic acid; the sum of k, n and p being an integer of from 5 to 14, and the sum of r and p being an integer of from 7 to 16.

2. An epoxycycloalkylalkanecarboxylic acid of formula I*

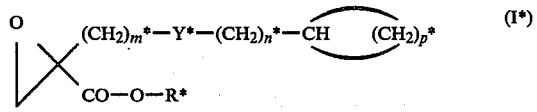

wherein R* denotes a hydrogen atom or a lower alkyl group, Y* denotes a methylene group, m* denotes an integer from 1 to 6, n* denotes the number 1 and p* denotes an integer from 4 to 7; and the sum of the numbers m*, n* and p* is an integer from 6 to 11; or a salt of the carboxylic acid.

3. A compound according to claim 2, characterized by formula I*, wherein R* denotes hydrogen, methyl or ethyl, Y* denotes methylene, m* denotes 2, 3 or 4, n* denotes 1 and p* denotes 5; or a salt of the carboxylic acid.

4. An epoxycycloalkylalkanecarboxylic acid of formula I**

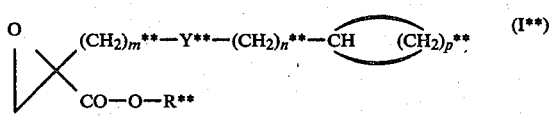

wherein R denotes a hydrogen atom or a lower alkyl group, Y denotes an oxygen atom, m denotes an integer from 2 to 6, n denotes an integer from 0 to 4 and p denotes an integer from 4 to 7; and the sum of the numbers m, n and p is an integer from 6 to 11; or a salt of the carboxylic acid.

5. A compound according to claim 4, characterized by formula I, wherein R denotes hydrogen, methyl or ethyl, Y denotes oxygen, m denotes an integer frm 2 to 5, n denotes an integer from 0 to 3, p denotes 5 and the sum of the numbers m and n is an integer from 3 to 5; or a salt of the carboxylic acid.

6. A compound according to claim 1 wherein t is 1.

7. A compound according to claim 1 wherein t is 2.

8. A compound according to claim 1 wherein each salt is a pharmacologically-acceptable salt.

9. The compound according to claim 1 which is 2-(5-cyclohexylpentyl)-oxirane-2-carboxylic acid ethyl ester.

10. The compound according to claim 1 which is 2-[2-(3-cyclohexylpropyloxy)-ethyl]-oxirane-2-carboxylic acid ethyl ester.

11. A medicament containing at least one compound according to claim 1 or 2 or 3 or 4 or 5.

12. A pharmaceutical preparation containing from 1 to 95% by weight of the total mixture of at least one compound according to claim 1 or 2 or 3 or 4 or 5 in admixture with at least one solid or liquid pharmaceutically acceptable carrier.

13. A process for prophylaxis of or for treating disease caused by a disturbance of metabolism of glucose or fat which comprises administering an effective amount of at least one compound of claim 1, 2, 3, 4 or 5 to a human or other animal subject to or afflicted with such disease.

* * * * *

UNITED STATES PATENT OFFICE
CERTIFICATE OF CORRECTION

PATENT NO. : 4,430,339
DATED : February 7, 1984
INVENTOR(S) : Klaus EISTETTER and Erich RAPP It is certified that error appears in the above-identified patent and that said Letters Patent are hereby corrected as shown below:

Column 1, in the formula at line 15, " 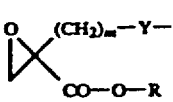 "

should read -- 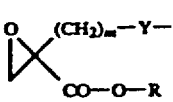 --.

Column 5, line 25, "unit" should read --A unit--. Column 9, line 20, "1979" should read --1979--. Column 10, line 60, "32" should read --32--; line 61, "33" should read --33--. Column 14, line 52, "ester" should read --ester,--. Column 19, line 50, "3,8" should read --3.8--. Column 20, line 17, "5,6" should read --5.6--. Column 21, line 23, "metaboically" should read --metabolically--; line 44, "14" should read --14--. Column 22, line 8, "aniamls" should read --animals--.

Signed and Sealed this

Twenty-seventh Day of November 1984

[SEAL]

Attest:

GERALD J. MOSSINGHOFF

Attesting Officer

Commissioner of Patents and Trademarks